United States Patent
Holmqvist (10) Patent No.: US 11,331,436 B2
(45) Date of Patent: May 17, 2022

(54) MEDICAMENT CONTAINER HOLDER FOR A MEDICAMENT DELIVERY DEVICE AND METHOD OF ASSEMBLING A MEDICAMENT DELIVERY DEVICE

(71) Applicant: SHL MEDICAL AG, Zug (CH)

(72) Inventor: Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 768 days.

(21) Appl. No.: 16/315,284

(22) PCT Filed: Jun. 28, 2017

(86) PCT No.: PCT/EP2017/066032
§ 371 (c)(1),
(2) Date: Jan. 4, 2019

(87) PCT Pub. No.: WO2018/015119
PCT Pub. Date: Jan. 25, 2018

(65) Prior Publication Data
US 2019/0307967 A1    Oct. 10, 2019

(30) Foreign Application Priority Data

Jul. 22, 2016  (EP) .................................... 16180922

(51) Int. Cl.
*A61M 5/32*    (2006.01)
*A61M 5/20*    (2006.01)
*A61M 5/24*    (2006.01)

(52) U.S. Cl.
CPC ............ *A61M 5/3202* (2013.01); *A61M 5/20* (2013.01); *A61M 5/24* (2013.01);
(Continued)

(58) Field of Classification Search
CPC .... A61M 5/3202; A61M 5/24; A61M 5/2033; A61M 5/20; A61M 2005/2407;
(Continued)

(56) References Cited

U.S. PATENT DOCUMENTS

| 5,865,805 A | 2/1999 | Ziemba |
| 2013/0253432 A1* | 9/2013 | Avery ..................... A61M 5/24 604/187 |
| 2014/0128843 A1 | 5/2014 | Baker et al. |

FOREIGN PATENT DOCUMENTS

| CN | 1946445 A | 4/2007 |
| CN | 101146562 A | 3/2008 |

(Continued)

OTHER PUBLICATIONS

International Search Report and Written Opinion for Int. App. No. PCT/EP2017/066032 dated Sep. 14, 2017.

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP (57) ABSTRACT

A medicament container holder for a medicament delivery device is presented having a C-shaped tubular body having a longitudinal gap extending along the entire axial extension of the C-shaped tubular body, which C-shaped tubular body is configured to be placed around a medicament container, wherein the C-shaped tubular body has a first axial end provided with an end flange extending radially inwards and configured to bear against a neck of a medicament container, and wherein the first axial end is provided with a lip extending proximally from the end flange.

16 Claims, 5 Drawing Sheets

(52) U.S. Cl.
CPC ............... *A61M 2005/244* (2013.01); *A61M 2005/2407* (2013.01); *A61M 2005/2414* (2013.01); *A61M 2005/2433* (2013.01); *A61M 2005/2485* (2013.01); *A61M 2207/00* (2013.01); *A61M 2209/082* (2013.01)

(58) Field of Classification Search
CPC .. A61M 2005/2414; A61M 2005/2433; A61M 2005/244; A61M 2005/2485; A61M 2207/00; A61M 2209/082
See application file for complete search history.

(56) References Cited

FOREIGN PATENT DOCUMENTS

| | | |
|---|---|---|
| CN | 102100572 A | 6/2011 |
| CN | 102170929 A | 8/2011 |
| CN | 103458945 A | 12/2013 |
| CN | 104093436 A | 10/2014 |
| CN | 104321102 A | 1/2015 |
| JP | H10-99434 A | 4/1998 |
| JP | 2012-519026 A | 8/2012 |
| JP | 2015-516849 A | 6/2015 |
| TW | 201509477 A | 3/2015 |
| WO | 2010/142598 A2 | 12/2010 |
| WO | 2011/124632 A1 | 10/2011 |
| WO | 2011/131776 A1 | 10/2011 |
| WO | 2012/064258 A1 | 5/2012 |
| WO | 2013/010893 A1 | 1/2013 |
| WO | 2013/156346 A2 | 10/2013 |
| WO | WO-2013156346 A2 * | 10/2013 ............. A61M 5/20 |
| WO | 2014/020000 A1 | 2/2014 |
| WO | 2014/023763 A1 | 2/2014 |
| WO | 2015/136564 A1 | 9/2015 |

\* cited by examiner

MEDICAMENT CONTAINER HOLDER FOR A MEDICAMENT DELIVERY DEVICE AND METHOD OF ASSEMBLING A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/066032 filed Jun. 28, 2017, which claims priority to European Patent Application No. 16180922.3 filed Jul. 22, 2016. The entire disclosure contents of these applications are herewith incorporated by reference into the present application.

TECHNICAL FIELD

The present disclosure generally relates to medical devices. In particular, it relates to a medicament container holder for a medicament delivery device, to a medicament delivery device comprising such a medicament container holder, and to a method of assembling a medicament delivery device.

BACKGROUND

A medicament delivery device may have a housing configured to receive a medicament container. For this purpose, the medicament delivery device may have a medicament container holder which holds the medicament container in place inside the housing.

WO 2013/156346 A2 discloses a medicament delivery device including a medicament container comprising a movable plunger, a neck portion and a delivery member unit. The medicament delivery device also has a housing having a proximal open end and an opposing distal open end and a drive unit arranged at the distal end of the housing and configured to apply a force on the movable plunger, and a C-shaped tubular body comprising a longitudinally extending slit/gap such that the C-shaped tubular body can be attached to the neck portion of the medicament container forming a container unit. The C-shaped tubular body further comprises inner support means configured to interact with the neck portion and with the delivery member unit of the medicament container such that the medicament container is prevented from being moved in relation to the C-shaped tubular body, after the medicament container is attached to the C-shaped tubular body, and outer support means configured to interact with corresponding support means of the housing such that the C-shaped tubular body is prevented from being moved in relation to the housing after the container unit is arranged within the housing through the distal open end.

SUMMARY

The C-shaped tubular body disclosed in WO 2013/156346 A2 can expand over the neck portion of the medicament container when pushed in the proximal direction during assembly, so that it moves distally from the neck portion and onto the main body of the medicament container. This could potentially change the position of the medicament container inside the housing, and thus of the delivery member, which could result in medicament expulsion at an incorrect penetration depth.

In view of the above, a general object of the present disclosure is to provide a medicament container holder for a medicament delivery device which solves or at least mitigates the problems of the prior art.

There is hence according to a first aspect of the present disclosure provided a medicament container holder for a medicament delivery device, comprising: a C-shaped tubular body having a longitudinal gap extending along the entire axial extension of the C-shaped tubular body, which C-shaped tubular body is configured to be placed around a medicament container, wherein the C-shaped tubular body has a first axial end provided with an end flange extending radially inwards and configured to bear against a neck of a medicament container, and wherein the first axial end is provided with a lip extending proximally from the end flange.

The lip is configured to move in radially below an outer distal end surface of a delivery member shield configured to be mounted to a medicament container for protecting the delivery member thereof. Thus, during assembly when a sub-assembly, formed by the delivery member shield, the medicament container and the medicament container holder, is being placed in a final assembly position inside the housing and the medicament container holder is pushed forward, towards a radial stop, a medicament container support or inner shoulder of the housing, the lip, arranged below the outer distal end surface of the delivery member shield will not allow radial expansion of the C-shaped tubular body because the radial deformation of the lip is delimited by the delivery member shield. Consequently, the C-shaped tubular body will also be prevented from radial expansion. Hereto, the medicament container holder, and thus the medicament container will be positioned correctly inside the housing after assembly.

According to one embodiment the first axial end has a first outer diameter and the lip has a proximal edge, defining the proximal end of the lip, having a second outer diameter, wherein the first outer diameter is larger than the second outer diameter.

According to one embodiment the C-shaped tubular body has an inner diameter and the lip has a proximal edge, defining the proximal end of the lip, having a second outer diameter, wherein the inner diameter is larger than the second outer diameter.

Furthermore, the lip is designed such that its radial thickness, its inner diameter and its outer diameter are dimensioned to allow the lip to extend in between two radial layers of a distal end of the delivery member shield.

According to one embodiment the lip is inclined and extends radially inwards in the proximal direction. The C-shaped body hence has a tapering shape in the proximal direction.

According to one embodiment the C-shaped tubular body is flexible. The C-shaped tubular body is thereby able to receive a medicament container through the gap or slit.

According to one embodiment the lip comprises a plurality of circumferentially extending separated lip sections. The C-shaped tubular body is thereby able to expand the gap for receiving a medicament container.

There is according to a second aspect of the present disclosure provided a medicament delivery device comprising: a housing configured to receive a medicament container, a medicament container support, and a medicament container holder according to the first aspect, wherein the medicament container holder is configured to bear against the medicament container support.

The medicament container support may be integrated with and provided on the inner surface of the housing, for example in the form of a flange or rib. Alternatively, the medicament container support may be formed by a distinct component such as an inner sleeve configured to be arranged inside the housing and configured to receive a medicament container.

One embodiment comprises a medicament container, wherein the medicament container holder is configured to be arranged around the medicament container to prevent the medicament container from proximal displacement in the housing.

According to one embodiment the medicament container is a syringe.

One embodiment comprises a delivery member shield having a flexible inner member configured to receive a needle of the syringe, and a rigid outer member configured to receive the flexible inner member, wherein the rigid outer member is configured to be linearly displaceable relative to the flexible inner member, and wherein the lip of the medicament container holder is configured to be received between the rigid outer member and the flexible inner member.

There is according to a third aspect of the present disclosure provided a method of assembling a medicament delivery device, comprising: a) providing a medicament container assembly including a medicament container having a delivery member and a delivery member shield covering the delivery member, b) providing, from a side perpendicular to the longitudinal axis of the medicament container, a medicament container holder as claimed in any of claims 1-6 around the medicament container by expanding the C-shaped tubular body, thereby snapping the medicament container holder onto the medicament container, and c) moving the medicament container linearly relative to the medicament container holder until the medicament container holder reaches the delivery member shield.

According to one embodiment in step c) the medicament container holder is maintained in a fixed position by a first assembly tool and the medicament container is moved relative to the medicament container holder by a second assembly tool.

One embodiment comprises, after step c), d) inserting the medicament container with the medicament container holder provided thereon into a housing of a medicament delivery device from a distal end opening of the housing.

According to one embodiment the medicament delivery device has a cap provided at the proximal end thereof and a medicament container support, wherein the method comprises e) moving the medicament container with the medicament container holder proximally in the housing until the delivery member shield engages with the cap and the medicament container holder bears against the medicament container support.

According to one embodiment the medicament container is a syringe comprising a needle and the delivery member shield comprises a flexible inner member covering the needle and a rigid outer member arranged around and linearly displaceable relative to the flexible inner member, wherein in step e) the rigid outer member moves over the lip.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a medicament container holder, refers to that end of the medicament container holder which is intended to be pointed towards the injection site during medicament administration, when the medicament container holder is properly installed in a medicament delivery device. The "distal end" is the opposite end relative to the proximal end. With "proximal direction" and, equivalently, "proximally" is meant a direction from the distal end towards the proximal end, along the central axis of the safety mechanism. With "distal direction" or "distally" is meant the opposite direction to "proximal direction".

The present disclosure relates to a medicament container holder for a medicament delivery device. The medicament container holder has a C-shaped tubular body provided with a longitudinal gap extending along the entire axial extension of the C-shaped tubular body. Due to the gap, the C-shaped tubular body obtains a C-shaped cross-section for any cross-section along the longitudinal extension of the C-shaped tubular body.

The C-shaped tubular body is flexible. The gap can thus be expanded so that the C-shaped body can receive a medicament container through the expanded gap. The C-shaped tubular body may for example be made of a plastic material or a metal, such as steel or aluminium.

The C-shaped tubular body has a proximal end and a distal end. The proximal end, or first axial end, has a radial stopper, an end flange, extending radially inwards. The end flange is configured to bear against the neck of a medicament container having been received by the C-shaped body to prevent movement of the medicament container in the proximal direction relative to the medicament container holder. The first axial end is furthermore provided with a lip protruding from the end flange, in particular in the proximal direction. The lip has a proximal edge forming the proximal edge of the C-shaped tubular body.

An example of a medicament container holder will now be described in the context of an exemplary medicament delivery device, with reference to FIGS. 1-9.

Figure 1:
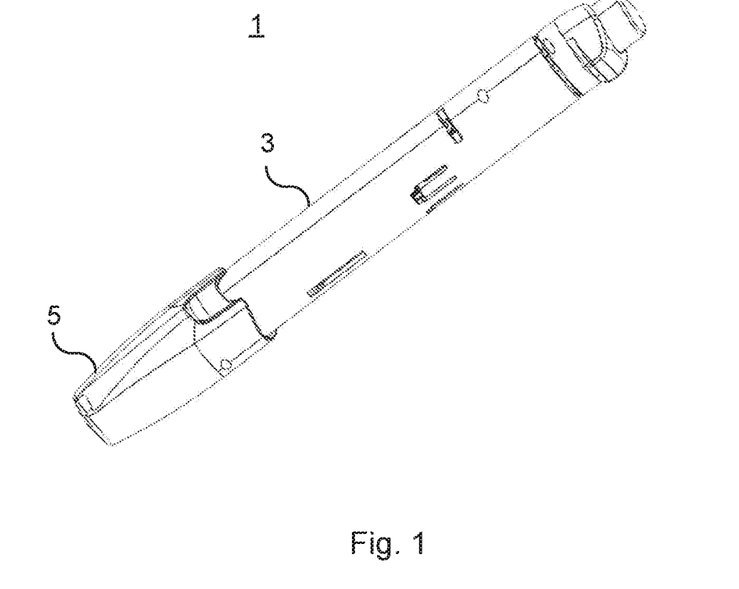
FIG. 1 is a perspective view of an example of a medicament delivery device.

FIG. 1 shows a perspective view of an example of a medicament delivery device 1. The medicament delivery device 1 has a housing 3 and a cap 5 provided at a proximal end of the housing 3. The exemplified medicament delivery device 1 is button-activated, but could alternatively be delivery member cover-activated, for example.

Figure 2:
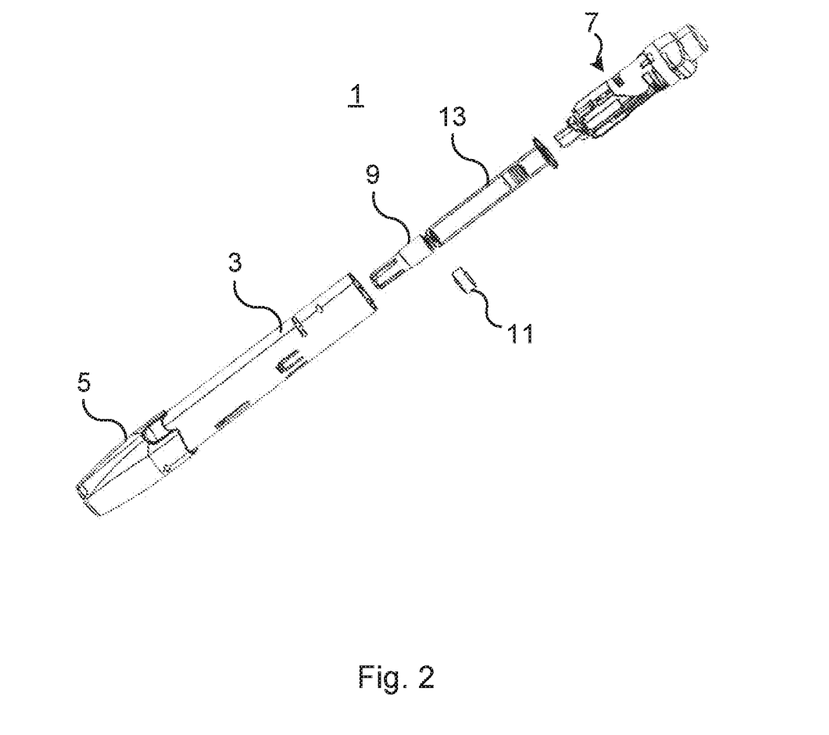
FIG. 2 is an exploded view of certain components of the medicament delivery device shown in FIG. 1.

The exploded view in FIG. 2 shows some internal components of the exemplified medicament delivery device 1. The medicament delivery device further comprises an activation assembly 7, for activating medicament expulsion, a delivery member shield 9, a medicament container holder 11, and a medicament container 13. These components are configured to be received inside the housing 3.

The medicament container holder 11 is configured to receive and hold the medicament container 13, and is further configured to bear against a medicament container support of the medicament delivery device 1, to prevent the medicament container 13 from moving proximally inside the housing 3 relative to the medicament container support.

The exemplified medicament container 13 is a syringe, and includes delivery member, in this case a needle. The delivery member shield 9 is configured to cover the delivery member. The delivery member shield 9 would typically be a rigid needle shield (RNS) but could be a flexible needle shield (FNS).

Figure 3:
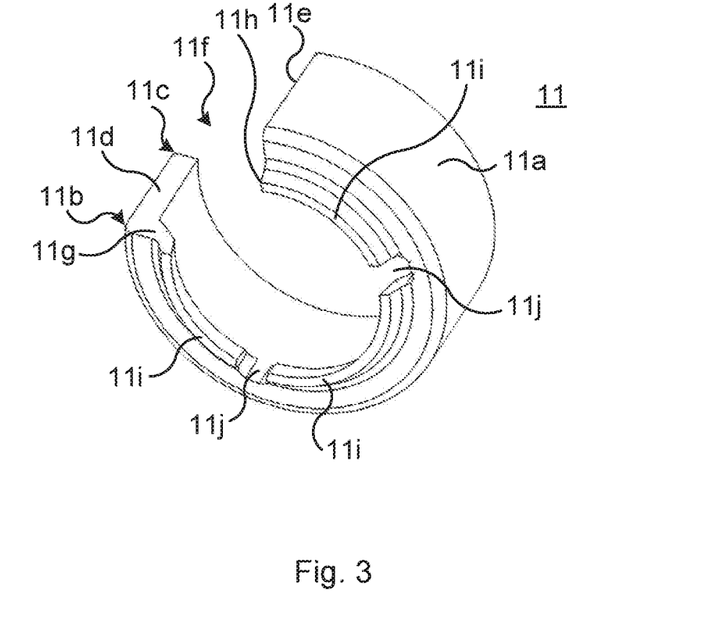
FIGS. 3 and 4 are perspective views of an example of a medicament container holder for a medicament delivery device.

FIG. 3 shows a perspective view of the medicament container holder 11. In particular, it shows the medicament container holder 11 from a proximal end thereof. The medicament container holder 11 has a C-shaped tubular body 11a. The C-shaped tubular body 11a has a proximal end, also referred to as a first axial end, 11b and a distal end 11c. The C-shaped tubular body 11a furthermore has a first end face 11d and a second end face 11e in the circumferential direction. The first end face 11d and the second end face 11e are thus spaced apart in the circumferential direction, forming a gap or slit 11f therebetween. The gap 11f extends along the entire longitudinal or axial extension of the C-shaped tubular body 11a.

The first axial end 11b has an end flange 11g, extending radially inwards, and a lip 11h extending proximally from the end flange 11g. The end flange 11g is configured to bear against a neck of the medicament container 13. The proximal end face of the lip 11h forms the proximal end face of the C-shaped tubular body 11a.

According to the example shown in FIG. 3, the lip 11h extends in the circumferential direction from the first end face 11d to the second end face 11e. In particular, the lip 11h covers the majority of the length, in the circumferential direction, between the first end face 11d and the second end face 11e.

According to the example in FIG. 3, the lip 11h has a plurality of separated lip sections 11i. The lip sections 11i are separated by axial slits 11j. The axial slits 11j facilitate expanding of the gap 11f, when the medicament container holder 11 is being placed around a medicament container 113 through the gap 11f.

Figure 4:
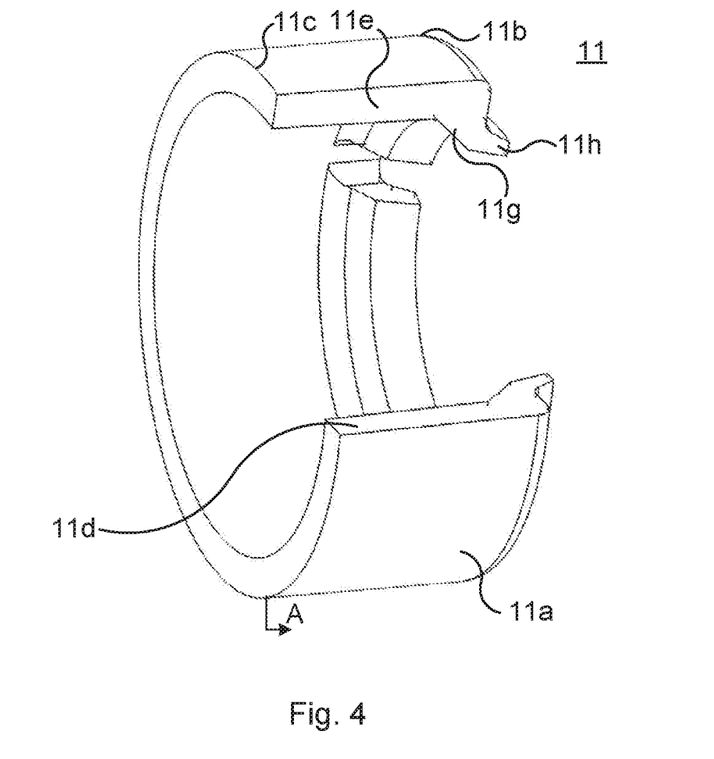
Figure 5:
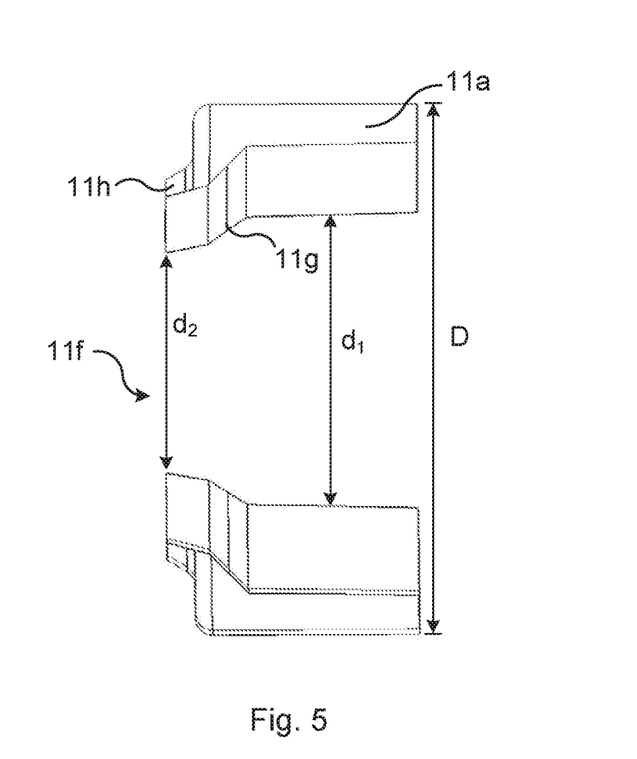
FIG. 5 is a cross-section of the medicament container holder along lines A-A shown in FIG. 4.

FIG. 4 shows another view of the medicament container holder 11, and in particular of the C-shaped tubular body 11a and FIG. 5 shows a cross-section of the C-shaped tubular body 11a along lines A-A. The C-shaped tubular body 11a has a first outer diameter D and an inner diameter d1. The lip 11h has a smaller inner diameter d2 than the remainder of the C-shaped tubular body 11a, i.e. an inner diameter d2 that is smaller than the inner diameter d1. In particular, the lip 11h which extends proximally from the end flange 11g is inclined, extending radially inwards in the proximal direction. The C-shaped tubular body 11a hence tapers in the proximal direction, due to the configuration of the lip 11h. Hereto, the inner diameter d2 of the C-shaped tubular body 11a is smaller at the proximal edge of the lip 11h than the inner diameter d1 is distally from the end flange 11g.

The radial surface extending between the lip 11h and the outer surface, defining the first outer diameter D, of the medicament container holder 11, acts as a support surface and is configured to bear against a medicament container support of the medicament delivery device 1 to prevent proximal movement of the medicament container holder 11 when arranged inside the housing 3.

Figure 6:
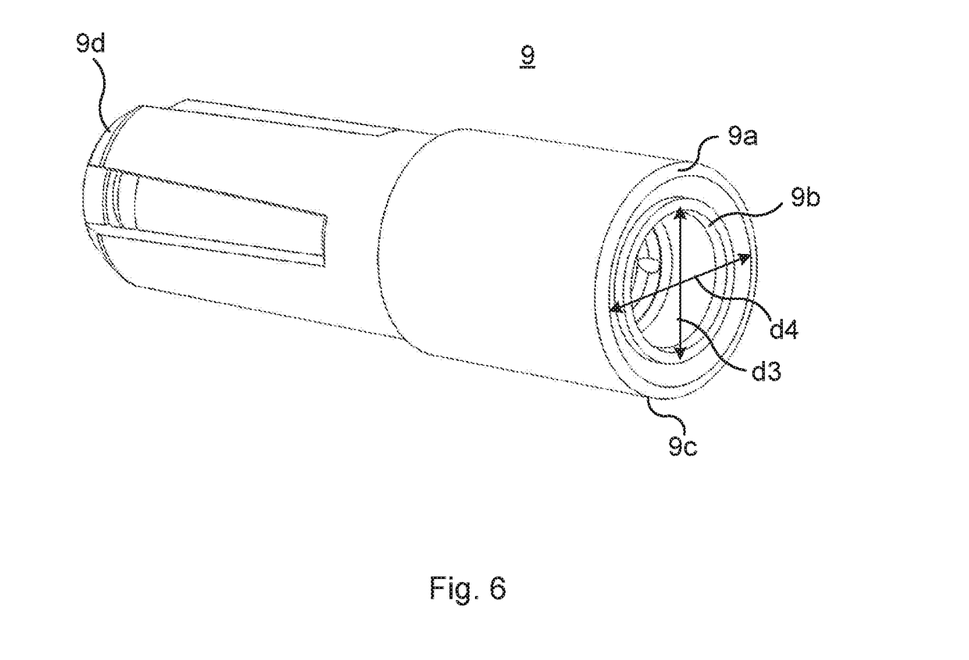
FIG. 6 is a perspective view of an example of a delivery member shield.

Turning now to FIG. 6, a perspective view of the delivery member shield 9 is shown. According to the present example, the delivery member shield 9 is a rigid needle shield. The delivery member shield 9 has a rigid outer member 9a and a flexible inner member 9b. The rigid outer member 9a is tubular and has a hollow interior. The flexible inner member 9b is also tubular. The rigid outer member 9a is configured to receive the flexible inner member 9b. Hereto, the outer diameter d3 of the flexible inner member 9b is smaller than the inner diameter d4 of the rigid outer member 9a.

The rigid outer member 9a is linearly displaceable relative to the flexible inner member 9b between a first position and a second position. The rigid outer member 9a is thus able to move slightly in the axial direction relative to the flexible inner member 9b.

The delivery member shield 9 furthermore has a distal end 9c and a proximal end 9d. The flexible inner member 9b is configured to receive the delivery member of the medicament container 13, in this example a needle and a syringe, respectively, from the distal end 9c.

Figure 7:
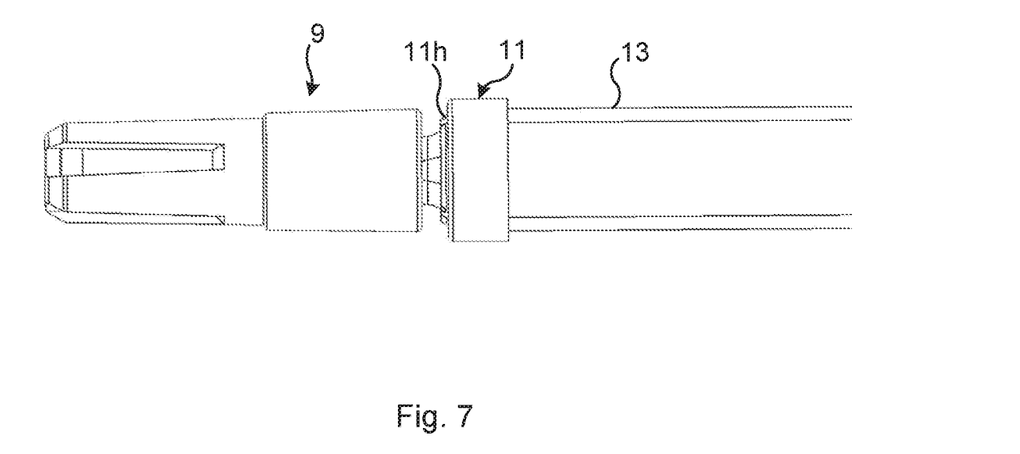
FIG. 7 is a side view of a sub-assembly including the medicament container holder and the delivery member shield.

With reference to FIG. 7, a sub-assembly including the medicament container 13, the medicament container holder 11 and the delivery member shield 9 is shown. The medicament container holder 11 is arranged around the medicament container 11. The delivery member shield 9 is furthermore assembled with the medicament container 13, so that it covers the delivery member.

Figure 8:
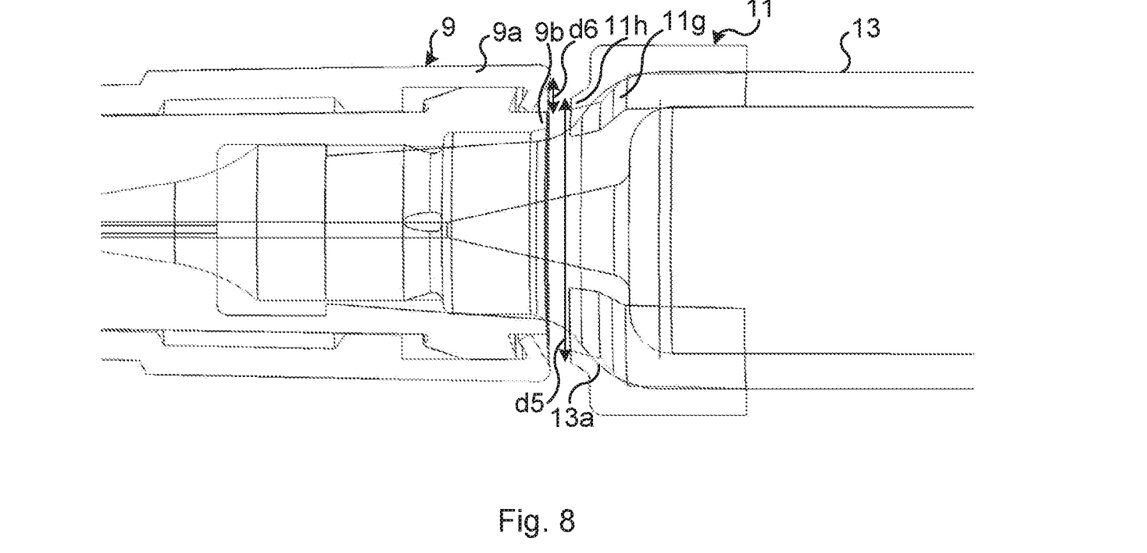
FIG. 8 shows a portion of a longitudinal section of the sub-assembly shown in FIG. 7.

FIG. 8 shows a cross-section of a portion of the sub-assembly shown in FIG. 7. The end flange 11 g has a distal wall which is inclined, successively reducing the inner diameter of the C-shaped tubular body 11 a in the proximal direction. The end flange 11g is configured to bear against the neck 13 a of the medicament container 13. The inner diameter d2 of the lip 11h is preferably larger than the outer diameter d3 of the flexible inner member 9b. Moreover, the outer diameter, a second outer diameter, d5 of the lip 11h is smaller than the inner diameter d4 of the rigid outer member 9a. The rigid outer member 9a and the flexible inner member 9b are furthermore arranged such that there is a distance d6 between the inner surface of the rigid outer member 9 a and the outer surface of the flexible inner member 9b. The radial thickness of the lip 11h is preferably smaller than the distance d6. Furthermore, the axial length of the lip 11h, i.e. the distance that it extends proximally from the remainder of the C-shaped tubular body is dimensioned so that the lip 11h is able to extend in between the rigid outer member 9a and the flexible inner member 9b, from a distal end thereof.

When the delivery member shield 9 has been placed onto the delivery member and the medicament container holder 11 is has been arranged around the medicament container 11, and the sub-assembly is brought inside the housing 3 and moved forward in the proximal direction, the delivery member shield 9 will eventually reach the inner surface of the cap 5. The delivery member shield 9, in particular the rigid outer member 9a which is linearly displaceable relative to the flexible inner member 9b, will then be pushed towards the neck 13a, causing the lip 11h to move in between the rigid outer member 9a and the flexible inner member 9b. As a result, this distally directed force will not expand the C-shaped tubular body 11a radially, because the lip 11h will be arranged between the rigid outer member 9a and the flexible inner member 9b, preventing radial expansion of the lip 11h, and therefore also of the entire C-shaped tubular body 11a.

Figure 9:
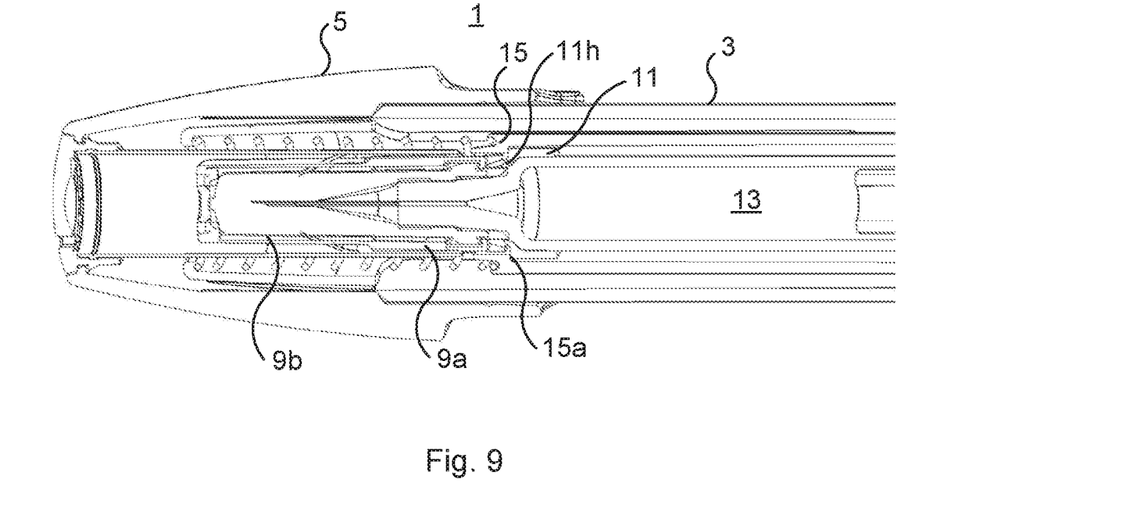
FIG. 9 depicts a longitudinal section of the medicament delivery device in FIG. 1.

FIG. 9 shows the sub-assembly mounted inside the medicament delivery device 1. According to the example shown in FIG. 9, the medicament delivery device 1 has an inner sleeve 15 arranged inside the housing 3. The inner sleeve 15 has a medicament container support 15a, in the form of a flange or shoulder in the proximal direction. The inner diameter of the inner sleeve 15 hence decreases in the proximal direction due to the medicament container support 15a. The medicament container holder 11 is configured to bear against the medicament container support 15a. The medicament container support 15a will thus prevent axial displacement of the medicament container holder 11 in the proximal direction relative to the medicament container support 15a, and thus also of the medicament container 13.

It may be noted that the medicament container support alternatively could be provided directly on the inner surface of the housing.

Figure 10:
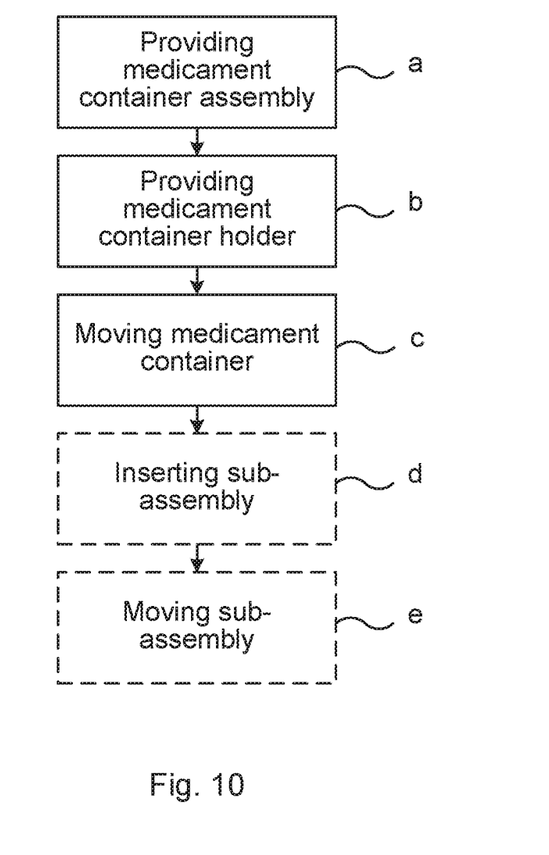
FIG. 10 is a flowchart of a method of assembling a medicament delivery device.

With reference to FIG. 10 a method of assembling a medicament delivery device, such as medicament delivery device 1, including the medicament container holder 11 will now be described.

In a step a) there is provided a medicament container 13 having a delivery member, and a delivery member shield 9 attached to the delivery member. The medicament container and the delivery member shield form a medicament container assembly.

In a step b) the medicament container holder 11 is provided onto the medicament container 13. In particular, the medicament container holder 11 is provided from a side perpendicular to the longitudinal axis of the medicament container 13 onto the medicament container 13, through the gap 11f. Hereto, the gap 11f is expanded, so that the medicament container holder 11 may be mounted onto the medicament container 13 from the side. The medicament container holder 11 is in this manner snapped onto the medicament container 13.

In a step c) the medicament container 13 is moved linearly relative to the medicament container holder 11 until the medicament container holder 11 reaches the delivery member shield 9. The medicament container holder 11 is hence moved towards the proximal end of the medicament container 13.

In step c) the medicament container holder 11 may be maintained in a fixed position by a first assembly tool while the medicament container 13 is moved relative to the medicament container holder 11 by a second assembly tool, until the medicament container holder 11 reaches the delivery member shield 9, and a proximal portion of the medicament container holder 11 is moved over the neck 13a of the medicament container 13. The lip 11h of the medicament container holder 11 may be pushed in between the rigid outer member 9a and the flexible inner member 9b of the delivery member shield 9, but does not necessarily have to be at this stage of assembly.

In a step d) the sub-assembly comprising the medicament container 13, the medicament container holder 11 and the delivery member shield 9 is inserted into the housing 3 of the medicament delivery device 1, from a distal end opening of the housing 3.

In a step e) the sub-assembly is moved proximally inside the housing 3 until the delivery member shield 9 engages with the cap 5, which is mounted to the proximal end of the housing 3, and the medicament container holder contacts the medicament container support 15a. During this stage, the rigid outer member 9a may be displaced distally relative to the flexible inner member 9b due to the delivery member shield 9 reaching an inner proximal end surface of the cap 5 and/or due to its engagement with the cap 5, causing the rigid outer member 9a to move over the lip 11h, which thus prevents radial expansion of the C-shaped tubular body 11a, even if the rigid outer member 9a is pressed distally towards the radial surface of the C-shaped tubular body 11a, arranged distally from the lip 11h.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament container holder for a medicament delivery device, comprising:
   a C-shaped tubular body having a longitudinal gap extending along an entire axial extension of the C-shaped tubular body, wherein the C-shaped tubular body is configured to be placed around a medicament container,
   wherein the C-shaped tubular body has a first axial end provided with an end flange extending radially inwards and configured to bear against a neck of the medicament container, wherein the first axial end is provided with a lip extending proximally from the end flange, and wherein the lip is inclined and extends radially inwards in the proximal direction.

2. The medicament container holder as claimed in claim 1, wherein the first axial end has a first outer diameter and the lip has a proximal edge, defining a proximal end of the lip, having a second outer diameter, wherein the first outer diameter is larger than the second outer diameter.

3. The medicament container holder as claimed in claim 1, wherein the C-shaped tubular body has an inner diameter and the lip has a proximal edge, defining the proximal end of the lip, having a second outer diameter, wherein the inner diameter is larger than the second outer diameter.

4. The medicament container holder as claimed in claim 1, wherein the C-shaped tubular body is flexible.

5. The medicament container holder as claimed in claim 1, wherein the lip comprises a plurality of circumferentially extending separated lip sections.

6. A method of assembling a medicament delivery device, comprising:
   a) providing a medicament container assembly including a medicament container having a delivery member and a delivery member shield covering the delivery member,
   b) providing, from a side perpendicular to the longitudinal axis of the medicament container, the medicament container holder according to claim 1 around the medicament container by expanding the C-shaped tubular body, thereby snapping the medicament container holder onto the medicament container, and
   c) moving the medicament container linearly relative to the medicament container holder until the medicament container holder reaches the delivery member shield.

7. The method as claimed in claim 6, wherein in step c) the medicament container holder is maintained in a fixed position by a first assembly tool and the medicament container is moved relative to the medicament container holder by a second assembly tool.

8. The method as claimed in claim 6, comprising, after step c), d) inserting the medicament container with the medicament container holder provided thereon into a housing of a medicament delivery device from a distal end opening of the housing.

9. The method as claimed in claim 8, wherein the medicament delivery device has a cap provided at the proximal end thereof and a medicament container support, wherein the method comprises e) moving the medicament container with the medicament container holder proximally in the housing until the delivery member shield engages with the cap and the medicament container holder bears against the medicament container support.

10. The method as claimed in claim 9, wherein the medicament container is a syringe comprising a needle and the delivery member shield comprises a flexible inner member covering the needle and a rigid outer member arranged around and linearly displaceable relative to the flexible inner member, wherein in step e) the rigid outer member moves over the lip.

11. A medicament delivery device comprising:
   a housing configured to receive a medicament container, wherein the medicament container is a syringe;
   a medicament container support;
   a delivery member shield comprising:
      a flexible inner member configured to receive a needle of the syringe, and a rigid outer member configured to receive the flexible inner member,
      wherein the rigid outer member is configured to be linearly displaceable relative to the flexible inner member, and
      wherein the lip of the medicament container holder is configured to be received between the rigid outer member and the flexible inner member; and
   a medicament container holder comprising:
      a C-shaped tubular body having a longitudinal gap extending along an entire axial extension of the C-shaped tubular body, which C-shaped tubular body is configured to be placed around the medicament container,
      wherein the C-shaped tubular body has a first axial end provided with an end flange extending radially inwards and configured to bear against a neck of the medicament container, and wherein the first axial end is provided with a lip extending proximally from the end flange,
      wherein the medicament container holder is configured to bear against the medicament container support,
      wherein the medicament container holder is configured to be arranged around the medicament container to prevent proximal displacement of the medicament container within the housing.

12. An assembly comprising:
   a syringe having a neck and a main body having an outer diameter; and
   a medicament container holder comprising:
   a C-shaped tubular body having a proximal end with a first inner diameter and a distal end having a second inner diameter that is larger than the first inner diameter, where the tubular body has a longitudinal gap defining a portion of the second inner diameter and extending from the distal end to the proximal end, where the first inner diameter is less than the outer diameter of the syringe,
   wherein the proximal end is provided with an end flange extending radially inwards and configured to bear against the neck of the syringe, and wherein the end flange comprises a segmented lip extending proximally from the end flange, and
   wherein the gap is configured to enlarge as the syringe is inserted into the medicament container holder.

13. The assembly of claim 12 where the segmented lip comprises lip sections separated by axial slits sized to assist in the enlargement of the gap.

14. The assembly of claim 13 where the segmented lip has a proximal edge defining a proximal end of the lip having an outer diameter, wherein the first inner diameter is larger than the outer diameter.

15. The assembly of claim 13 where the lip is inclined and extends radially inwards in the proximal direction.

16. The assembly of claim 12, where the C-shaped tubular body is comprises of a flexible material.

* * * * *